US012636037B2

(12) United States Patent
Xia et al.

(10) Patent No.: US 12,636,037 B2
(45) Date of Patent: May 26, 2026

(54) CIRCUMCISION EQUIPMENT

(71) Applicant: Wuhu ShangRing Technology Co., Ltd, Wuhu (CN)

(72) Inventors: Shujie Xia, Shanghai (CN); Huarong Yu, Beijing (CN); Jingjing Shang, Wuhu (CN); Jianzhong Shang, Wuhu (CN)

(73) Assignee: Wuhu ShangRing Technology Co., Ltd., Wuhu (CN)

( * ) Notice: Subject to any disclaimer, the term of this patent is extended or adjusted under 35 U.S.C. 154(b) by 91 days.

(21) Appl. No.: 18/624,114

(22) Filed: Apr. 2, 2024

(65) Prior Publication Data

US 2024/0238005 A1      Jul. 18, 2024

Related U.S. Application Data

(60) Division of application No. 16/531,139, filed on Aug. 5, 2019, now Pat. No. 11,980,390, and a continuation (Continued)

(30) Foreign Application Priority Data

| | | |
|---|---|---|
| Feb. 4, 2017 | (CN) | 201710063339.X |
| Feb. 4, 2017 | (CN) | 201710063340.2 |
| Feb. 4, 2017 | (CN) | 201710065136.4 |
| Feb. 4, 2017 | (CN) | 201710065137.9 |
| Feb. 4, 2017 | (CN) | 201710065138.3 |
| Feb. 4, 2017 | (CN) | 201710065139.8 |
| Feb. 4, 2017 | (CN) | 201710065140.0 |
| Feb. 4, 2017 | (CN) | 201710065146.8 |
| Feb. 4, 2017 | (CN) | 201710065147.2 |
| Feb. 4, 2017 | (CN) | 201710065148.7 |
| Feb. 4, 2017 | (CN) | 201710065149.1 |
| Feb. 4, 2017 | (CN) | 201710065150.4 |
| Feb. 4, 2017 | (CN) | 201720109034.3 |
| Apr. 18, 2017 | (CN) | 201710250780.9 |
| Apr. 18, 2017 | (CN) | 201710250951.8 |

(Continued)

(51) Int. Cl.
*A61B 17/326* (2006.01)
*A61B 17/068* (2006.01)
(Continued)

(52) U.S. Cl.
CPC ........ *A61B 17/326* (2013.01); *A61B 17/0682* (2013.01); *A61B 17/072* (2013.01);
(Continued)

(58) Field of Classification Search
CPC .............. A61B 17/326; A61B 17/0682; A61B 17/1155
See application file for complete search history.

(56) References Cited

U.S. PATENT DOCUMENTS

| | | | | |
|---|---|---|---|---|
| 5,467,911 A | * | 11/1995 | Tsuruta | A61B 17/0684 227/19 |
| 2004/0153124 A1 | * | 8/2004 | Whitman | A61B 17/07207 606/219 |

FOREIGN PATENT DOCUMENTS

CN          204890072      * 12/2015

* cited by examiner

*Primary Examiner* — Thomas Mcevoy
(74) *Attorney, Agent, or Firm* — JEEN IP LAW, LLC

(57)          ABSTRACT

The present invention relates to surgical devices, particularly to a circumcision apparatus, enable the circumcision apparatus to be suitable for different surgery objects and environments.

20 Claims, 10 Drawing Sheets

Related U.S. Application Data of application No. PCT/CN2018/074988, filed on Feb. 1, 2018.

(30)     Foreign Application Priority Data

| | | |
|---|---|---|
| Apr. 19, 2017 | (CN) | .......................... 201710254989.2 |
| Apr. 19, 2017 | (CN) | .......................... 201710255021.1 |
| Apr. 19, 2017 | (CN) | .......................... 201710255023.0 |
| Apr. 19, 2017 | (CN) | .......................... 201710255025.X |
| Apr. 24, 2017 | (CN) | .......................... 201710273894.5 |
| Apr. 24, 2017 | (CN) | .......................... 201710273895.X |
| Apr. 24, 2017 | (CN) | .......................... 201710274306.X |
| Apr. 24, 2017 | (CN) | .......................... 201710274307.4 |
| Apr. 24, 2017 | (CN) | .......................... 201710274308.9 |
| Apr. 24, 2017 | (CN) | .......................... 201710274309.3 |
| Apr. 24, 2017 | (CN) | .......................... 201710274396.2 |
| Apr. 24, 2017 | (CN) | .......................... 201710274397.7 |
| Apr. 24, 2017 | (CN) | .......................... 201710274398.1 |
| Apr. 24, 2017 | (CN) | .......................... 201710274399.6 |
| Apr. 24, 2017 | (CN) | .......................... 201710274400.5 |
| Apr. 24, 2017 | (CN) | .......................... 201710274426.X |
| Aug. 18, 2017 | (CN) | .......................... 201710709597.0 |

(51) Int. Cl.

| | |
|---|---|
| *A61B 17/072* | (2006.01) |
| *A61B 17/115* | (2006.01) |
| *A61B 90/00* | (2016.01) |
| *A61B 17/00* | (2006.01) |

(52) U.S. Cl.
CPC .......... *A61B 17/1155* (2013.01); *A61B 90/08* (2016.02); *A61B 2017/00561* (2013.01); *A61B 2017/07228* (2013.01); *A61B 2017/07285* (2013.01); *A61B 2090/0811* (2016.02)

7-2-1

7-2

2

1-4

1-3-1

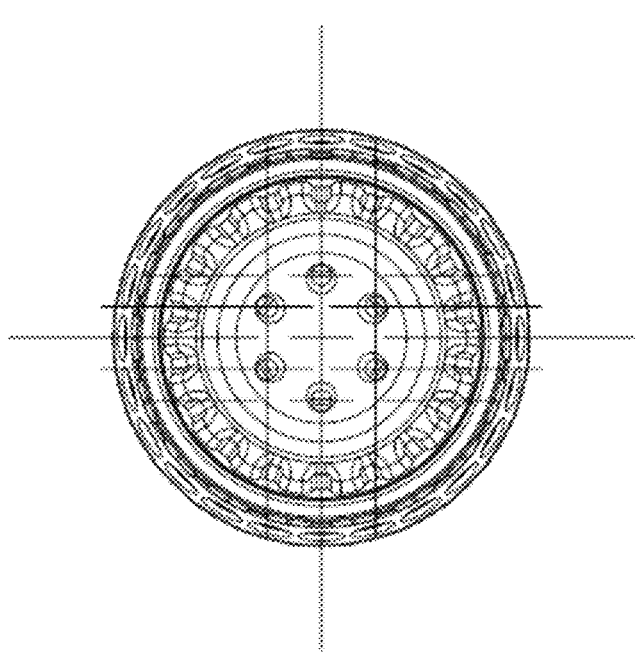
Fig. 6
Fig. 7
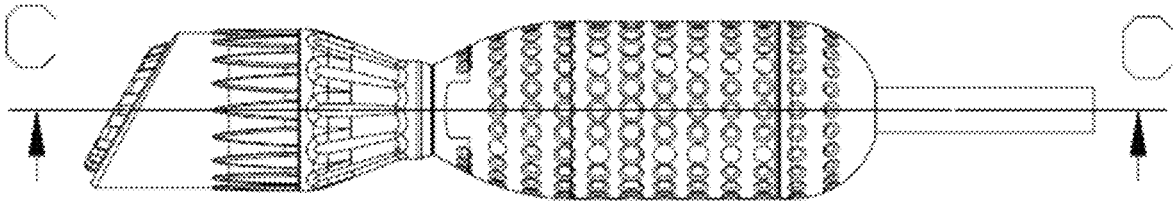
Fig. 8

CIRCUMCISION EQUIPMENT

CROSS REFERENCE TO RELATED APPLICATIONS

The present application is a Divisional Applications of U.S. patent application Ser. No. 16/531,139 filed on Aug. 5, 2019, which is a Continuation Application of PCT Application No. PCT/CN2018/074988 filed on Feb. 1, 2018, which claims the benefit of Chinese patents application Nos. 201710063339.X, 201710065146.8, 201710065140.0, 201710065139.8, 201710065138.3, 201710065150.4, 201710065149.1, 201710065148.7, 201710065147.2, 201710063340.2, 201710065137.9, 201710065136.4, 201720109034.3 filed on Feb. 4, 2017, Chinese Patent Application Nos. 201710250780.9 and 201710250951.8 filed on Apr. 18, 2017, Chinese Patent Application Nos. 201710254989.2, 201710255021.1, 201710255023.0 and 201710255025.X filed on Apr. 19, 2017, Chinese Patent Application Nos. 201710274426.X, 201710274400.5, 201710274399.6, 201710274398.1, 201710274397.7, 201710274396.2, 201710274309.3, 201710274308.9, 201710274307.4, 201710274306.X, 201710273895.X and 201710273894.5 filed on Apr. 24, 2017, and Chinese Patent Application No. 201710709597.0 filed on Aug. 18, 2017. All the above are hereby incorporated by reference.

FIELD OF THE INVENTION

The present invention relates to surgical devices, particularly to a circumcision apparatus and more particularly to a built-in electric circumcision device and a valgus electric circumcision device.

BACKGROUND OF THE INVENTION

Refer to the built-in electric circumcision device and a valgus electric circumcision device. The redundant prepuce or phimosis is one of the causes of male urinary system infections and sexually transmitted diseases. The redundant prepuce or phimosis can cause urinary tract infections, resulting in chronic prostatitis, with a series of symptoms, such as pains in back and waist, impotence and premature ejaculation. Therefore, the removal of the redundant prepuce is a good way to prevent these diseases.

Traditionally, surgical removal of the phimosis or redundant prepuce has the main technical points of removal of excess prepuce, hemostasis, and apposition suture of cut edges to skin. A postoperative patient cannot move around, suffers unbearable pain in each change of ointment and endures huge pain when stitches are taken out finally. In addition, incomplete ligating hemostasis will cause prepuce hematoma, thus requiring a surgical treatment again. Furthermore, since the prepuce removal and the hemostasis process are performed separately, the operation time is prolonged, and the patient's panic is exacerbated.

A therapeutic method of applying a laser and high-frequency electric surgical knife technology to circumcision has been developed at present. Although this therapeutic method substitutes for scissors cutting and makes a bleeding spot coagulated, the patient's tissues will be burnt and susceptible to infection.

Then, a circumcision device in which a prepuce incision is sutured using suturing nails at one time was developed in this field. However, all of the circumcision devices in the prior art are manually driven or remotely pedal-driven. The surgical operation, especially the time and force for tapping out a U-nail, is very unstable due to features of manual drive. If being applied with excessive force, the U-nail may clamp off the prepuce tissue to cause failure of the surgery; or if the applied force is insufficient, the tapping of the U-nail may be incomplete, resulting in failure of both hemostasis and the surgery. In manual drive, the circumcision device has to be provided with two sets of driving structures to drive a circumcision knife and the U-nail, respectively. Once the two driving structure are uncooperative, phenomena will appear that the circumcision by the circumcision knife is completed while the U-nail fails to stop bleeding or the U-nail is tapped out while the circumcision is not completed, any of which has a great risk and brings pain to a patient.

SUMMARY OF THE INVENTION

Refer to the built-in electric circumcision device and a valgus electric circumcision device.

For the above problems in the prior art, an object of the present invention is to provide an electric circumcision device, and particularly relates to a built-in electric circumcision device and a valgus electric circumcision device. In the electric circumcision device, a U-nail is driven by a motor, so that instability and various risks caused by manual drive are avoided. The specific technical solutions are as follows.

A built-in electric circumcision device comprises a motor, a thrust tube, a U-nail top ring and a circumcision cover, wherein the motor is connected to or in contact with the thrust tube, and is configured to drive the thrust tube forward; the thrust tube is connected to or in contact with the U-nail top ring, and is configured to thrust the U-nail top ring forward; and the motor is connected to or in contact with the circumcision cover.

Further, the thrust tube is a hollow cylinder with a first ring-shaped cross section, wherein the ring-shaped end of the front end of the hollow cylinder is connected to or in contact with the rear end of the U-nail top ring; and/or the U-nail top ring is configured to push out a U-nail from a U-nail groove of the circumcision device.

Further, the motor has an end thread, and is connected to or in contact with the circumcision cover via the end thread.

Further, the motor has a connecting rod on which the thread is arranged.

Further, the circumcision cover comprises a positioning rod connected to or in contact with the connecting rod or the thread; and/or a positioning groove is formed in the positioning rod, and is provided with an inner thread threadedly matched with the thread.

Further, the built-in electric circumcision device also comprises a motor front shell and a comprehensive cover; the front end of the motor front shell is connected to the rear end of the comprehensive cover; and/or the cross section of the front end of the motor front shell is in the shape of a second ring capable of accommodating the first ring.

Further, the built-in electric circumcision device also comprises a motor rear shell cooperating with the motor front shell to form a space for accommodating the motor.

Further, the built-in electric circumcision device also comprises a cable which is connected to and supplies power to the motor.

Further, the built-in electric circumcision device also comprises a switch which is arranged on the motor rear shell or the motor front shell or the comprehensive cover, and is configured to control the powering on or off, and/or a driving distance, and/or a driving speed of the motor.

Further, a cable hole is formed in the motor rear shell; and the cable passes through the cable hole and is connected to the motor.

According to another solution of the present invention, there is provided a valgus electric circumcision device, comprising a motor, a thrust tube and a U-nail top ring, wherein the motor is connected to or in contact with the thrust tube, and is configured to drive the thrust tube forward; and the thrust tube is connected to or in contact with the U-nail top ring, and is configured to thrust the U-nail top ring forward.

Further, the valgus electric circumcision device comprises an inner comprehensive cover; and the motor is connected to or in contact with the inner comprehensive cover.

Further, the thrust tube is a hollow cylinder with a first ring-shaped cross section, wherein the ring-shaped end of the front end of the hollow cylinder is connected to or in contact with the rear end of the U-nail top ring; and/or the U-nail top ring is configured to push out a U-nail from a U-nail groove of the circumcision device.

Further, the motor has a connecting rod and an end thread on the connecting rod, and is connected to or in contact with the inner comprehensive cover via the end thread.

Further, the inner comprehensive cover comprises a positioning rod; and a positioning groove is formed in the positioning rod, and is provided with an inner thread threadedly matched with the end thread.

Further, the valgus electric circumcision device also comprises a motor front shell and a comprehensive cover in which the inner comprehensive cover is located; the front end of the motor front shell is connected to the rear end of the comprehensive cover; and/or the cross section of the front end of the motor front shell is in the shape of a second ring capable of accommodating the first ring.

Further, the valgus electric circumcision device also comprises a motor rear shell cooperating with the motor front shell to form a space for accommodating the motor.

Further, the valgus electric circumcision device also comprises a cable which is connected to and supplies power to the motor.

Further, the valgus electric circumcision device also comprises a switch which is arranged on the motor rear shell or the motor front shell or the comprehensive cover, and is configured to control the powering on or off and/or a driving distance and/or a driving speed of the motor.

Further, a cable hole is formed in the motor rear shell; and the cable passes through the cable hole and is connected to the motor.

Compared with the prior art, the electric circumcision device provided by the present invention uses the motor to drive the U-nail to avoid instability and various risks caused by manual drive. Particularly, the driving force of the U-nail by the motor is adjustable and stable, so that phenomena are avoided that the U-nail applied with excessive force clamps off the prepuce tissue to cause failure of the surgery and incomplete tapping of the nail causes failure of hemostasis as the force applied to the U-nail is insufficient. Meanwhile, the switch is adopted to adjust the driving distance and speed to enable the electric circumcision device to be suitable for different surgery objects and environments. In addition, a driving structure and an actuating structure driven by a motor are adopted, so that manual driving can be omitted and the risk caused by unsynchronized running of the above two driving structures is prevented. After adopting the motor for driving, the overall appearance of the circumcision device is simple, and components such as a handle hinge and the like are omitted, so that the mold preparation cost and the production cost are significantly reduced.

BRIEF DESCRIPTION OF THE DRAWINGS

Refer to the built-in electric circumcision device and a valgus electric circumcision device.

FIG. 6 shows a front end view of the built-in circumcision device.

FIG. 7 shows an overall appearance view of a valgus circumcision device.

FIG. 8 shows an overall structure view of the valgus circumcision device.

Figure 1:
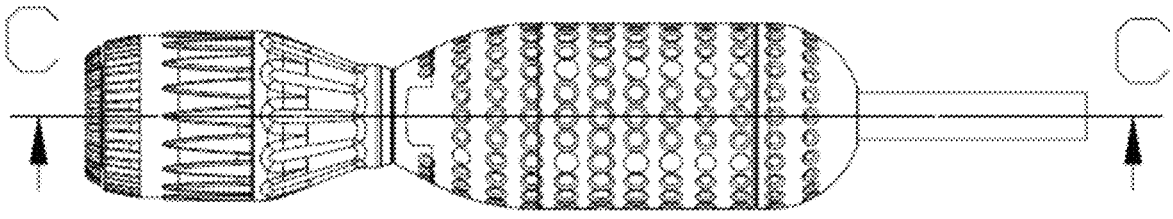
FIG. 1 shows an overall appearance view of a built-in circumcision device.
Figure 2:
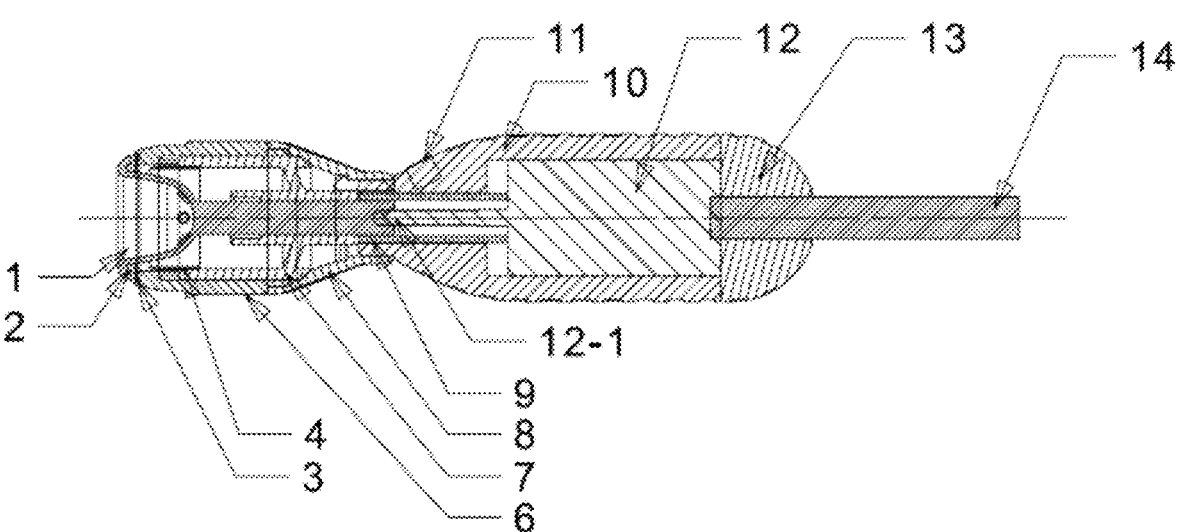
FIG. 2 shows an overall structure view of the built-in circumcision device.
Figure 3:
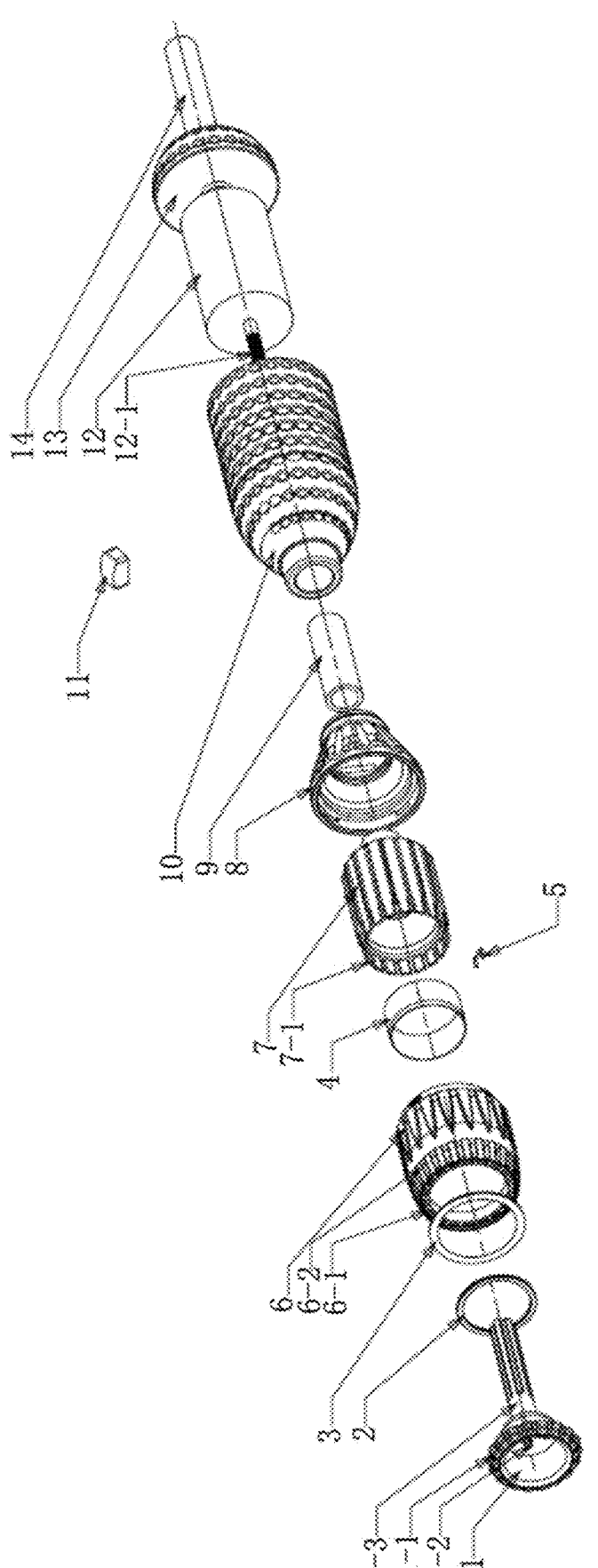
FIG. 3 shows a structurally exploded view of the built-in circumcision device.

The reference numerals in the above figures are shown as follows: 1: circumcision cover; 1-1: blood vessel corresponding groove; 1-2: negative pressure hole; 1-3: positioning rod; 1-3-1: positioning groove; 1-4: U-nail seat; 2: circumcision knife gasket; 3: U-nail backing ring; 4: circumcision knife; 5: U-nail; 6: comprehensive cover; 7: U-nail top ring; 7-1: U-nail top column; 7-2: positioning hole; 7-2-1: positioning groove; 8: comprehensive cover (rear); 9: thrust tube; 10: motor front shell; 11: switch; 12: motor; 12-1: thread; 13: motor rear shell; and 14: cable.

Figure 12:
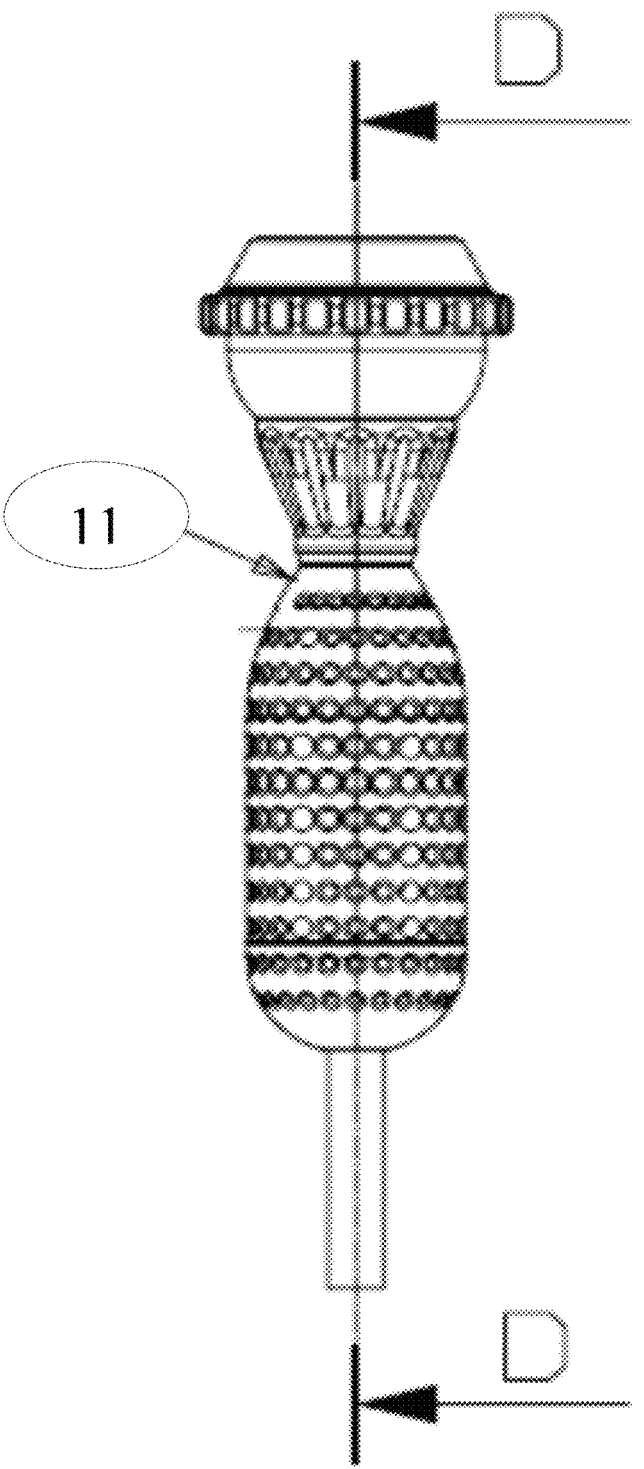

FIG. 12 shows another overall appearance view of the valgus circumcision device.

Figure 13:
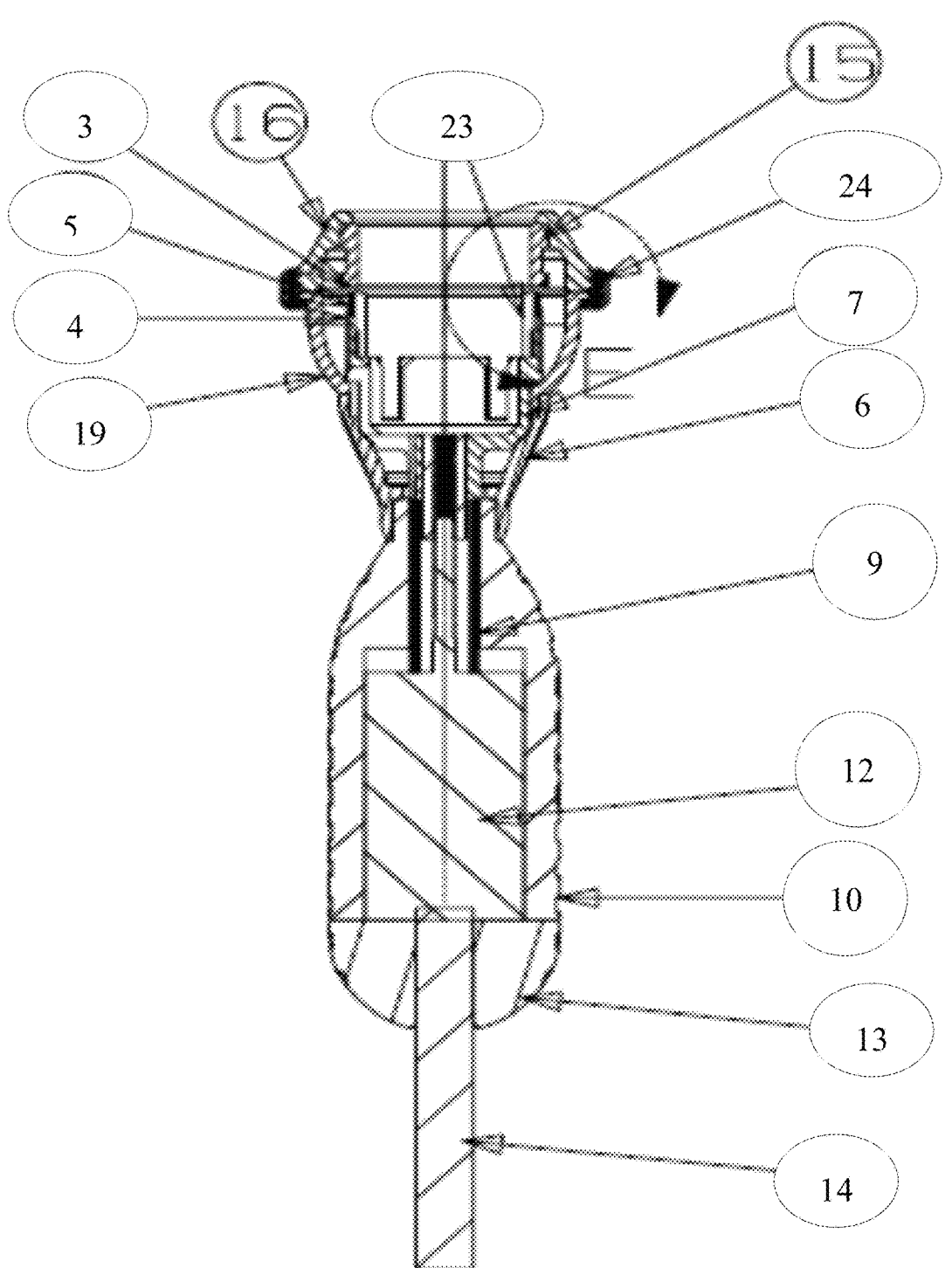

FIG. 13 shows another structure view of the valgus circumcision device.

Figure 14:
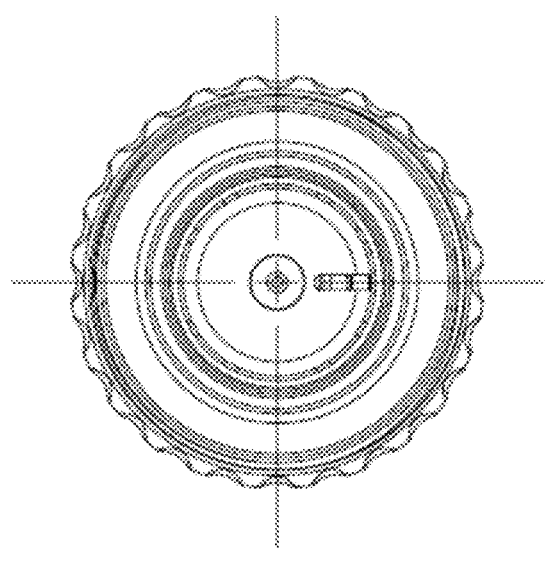

FIG. 14 shows a top view of the valgus circumcision device.

Figure 15:
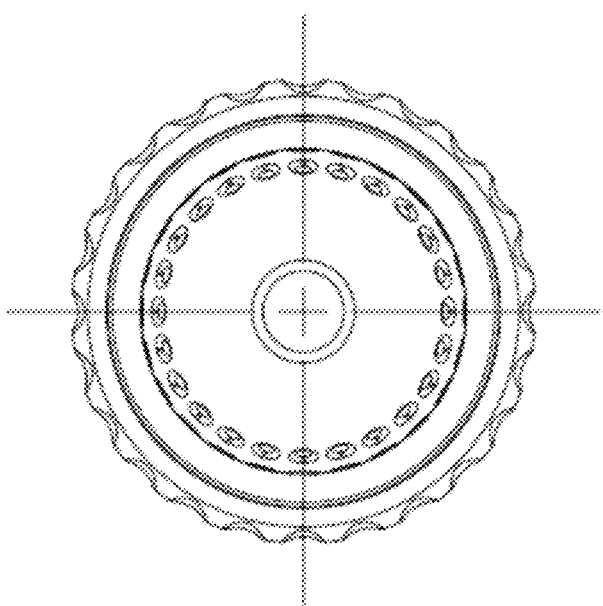

FIG. 15 shows a bottom view of the valgus circumcision device.

Figure 16:
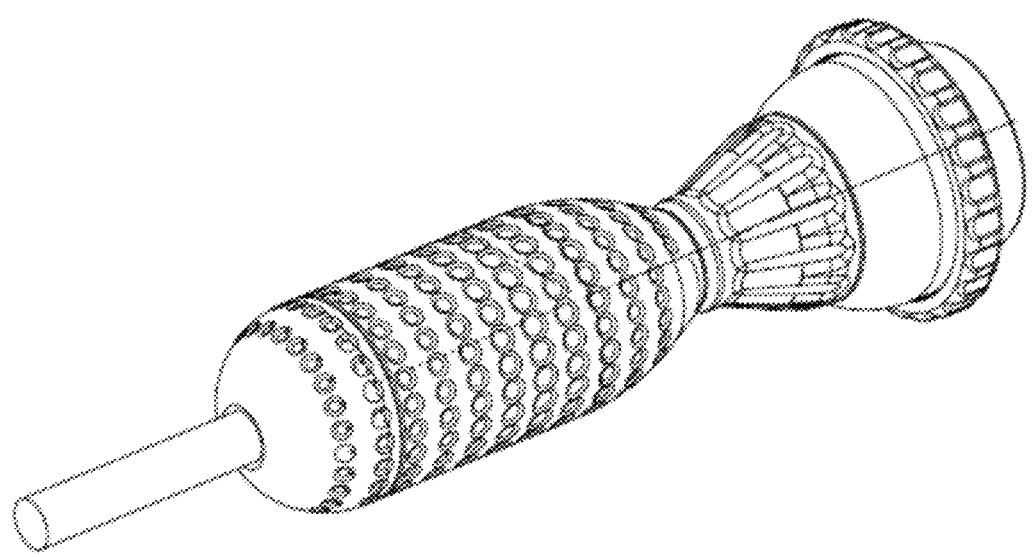

FIG. 16 shows a stereoscopic view of the valgus circumcision device.

Figure 17:
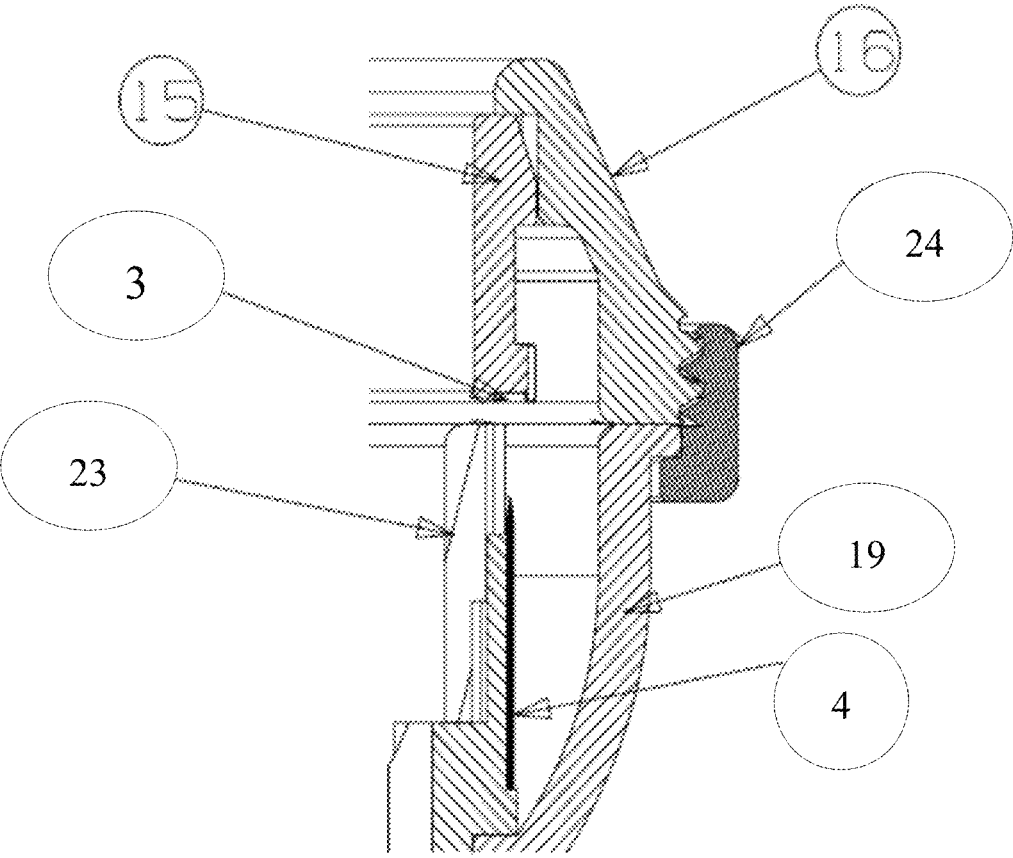

FIG. 17 shows an enlarged view of the portion E of the valgus circumcision device shown in FIG. 13.

The reference numerals in the above figures are shown as follows: 14: cable; 13: motor rear shell; 10: motor front shell; 12: motor; 11: switch; 9: thrust tube; 6: comprehensive cover (front); 7: U-nail top ring; 19: lower cover; 5: U-nail; 4: circumcision knife; 3: U-nail backing ring; 23: inner comprehensive cover; 24: locking ring; 15: inner ring; and 16: upper cover.

SPECIFIC DESCRIPTION OF THE EMBODIMENTS

Refer to the built-in electric circumcision device and a valgus electric circumcision device.

The present invention will be described in detail below with reference to the accompanying drawings. FIG. 1 to FIG. 11 show preferred embodiments in various embodiments of the present invention.

FIG. 1 to FIG. 6 show overall appearance views of a built-in circumcision device. It can be seen after adopting a motor for driving, the overall appearance of the circumcision device is simple, and components such as a handle hinge and the like are omitted, so that the mold preparation cost and the production cost are significantly reduced.

FIGS. 2, 3, 8 and 9 are structural views and structurally exploded views of the circumcision device, respectively. In the structure shown in these figures, 1 represents a circumcision cover, 1-1 a blood vessel corresponding groove, 1-2 a negative pressure hole, 1-3 a positioning rod, 1-3-1 a positioning groove, 1-4 a U-nail seat, 2 a circumcision knife gasket, 3 a U-nail backing ring, 4 a circumcision knife, 5 a U-nail, 6 a comprehensive cover (front), 7 a U-nail top ring, 7-1 a U-nail top column, 7-2 a positioning hole, 7-2-1 a positioning groove, 8 a comprehensive cover (rear), 9 a thrust tube, 10 a motor front shell, 11 a switch, 12 a motor, 12-1 a thread, 13 a motor rear shell, and 14 a cable. The related driving parts, actuating parts, circumcision parts and the like are of common structures in the art. Referring to the drawings, the position relations and connecting relations are both clear; various combinations in the prior art can be adopted; and the details will not be repeated here. The built-in electric circumcision device comprises a motor 12, a thrust tube 9, a U-nail top ring 7 and a circumcision cover 1, wherein the motor 12 is connected to the thrust tube 9, and is configured to drive the thrust tube 9 forward; the thrust tube 9 is connected to the U-nail top ring 7, and is configured to thrust the U-nail top ring 7 forward; the motor 12 is connected to the circumcision cover 1; the thrust tube 9 is a hollow cylinder with a first ring-shaped cross section, and the ring-shaped end of the front end of the hollow cylinder is connected to the rear end of the U-nail top ring 7; the U-nail top ring 7 is configured to push out a U-nail from a U-nail groove of the circumcision device; the motor 12 has an end thread 12-1, and is connected to the circumcision cover 1 via the end thread 12-1; the motor 12 has a connecting rod on which the thread 12-1 is arranged; the circumcision cover 1 comprises a positioning rod 1-3 connected to the thread 12-1; positioning grooves 7-2-1 are formed in the positioning rod 1-3, and are provided with inner threads; and the inner threads and the thread 12-1 are threadedly matched with each other.

The built-in electric circumcision device further comprises a motor front shell 10 and a comprehensive cover 8. The front end of the motor front shell 10 is connected to the rear end of the comprehensive cover 8. The cross section of the front end of the motor front shell 10 is in the shape of a second ring capable of accommodating the first ring. The built-in electric circumcision device also comprises: a motor rear shell 13 cooperating with the motor front shell 10 to form a space for accommodating the motor 12, a cable 14 which is connected to and supplies power to the motor 12, and a switch 11 arranged on the motor front shell 10 and configured to control the powering on or off and a driving distance and speed of the motor 12. A cable hole 13 is formed in the motor rear shell 13. The cable 14 passes through the cable hole and is connected to the motor 12.

Figure 4:
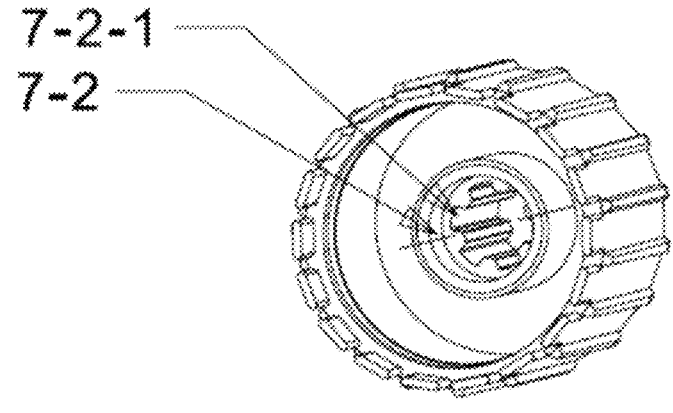
FIG. 4 shows a structural view of a U-nail top ring of the built-in circumcision device.
Figure 5:
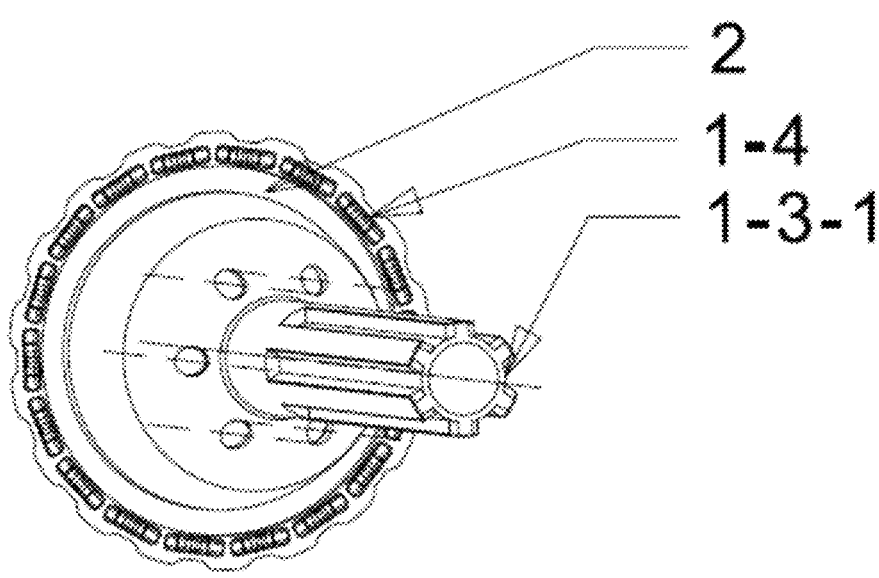
FIG. 5 shows a structural view of a circumcision cover of the built-in circumcision device.
Figure 9:
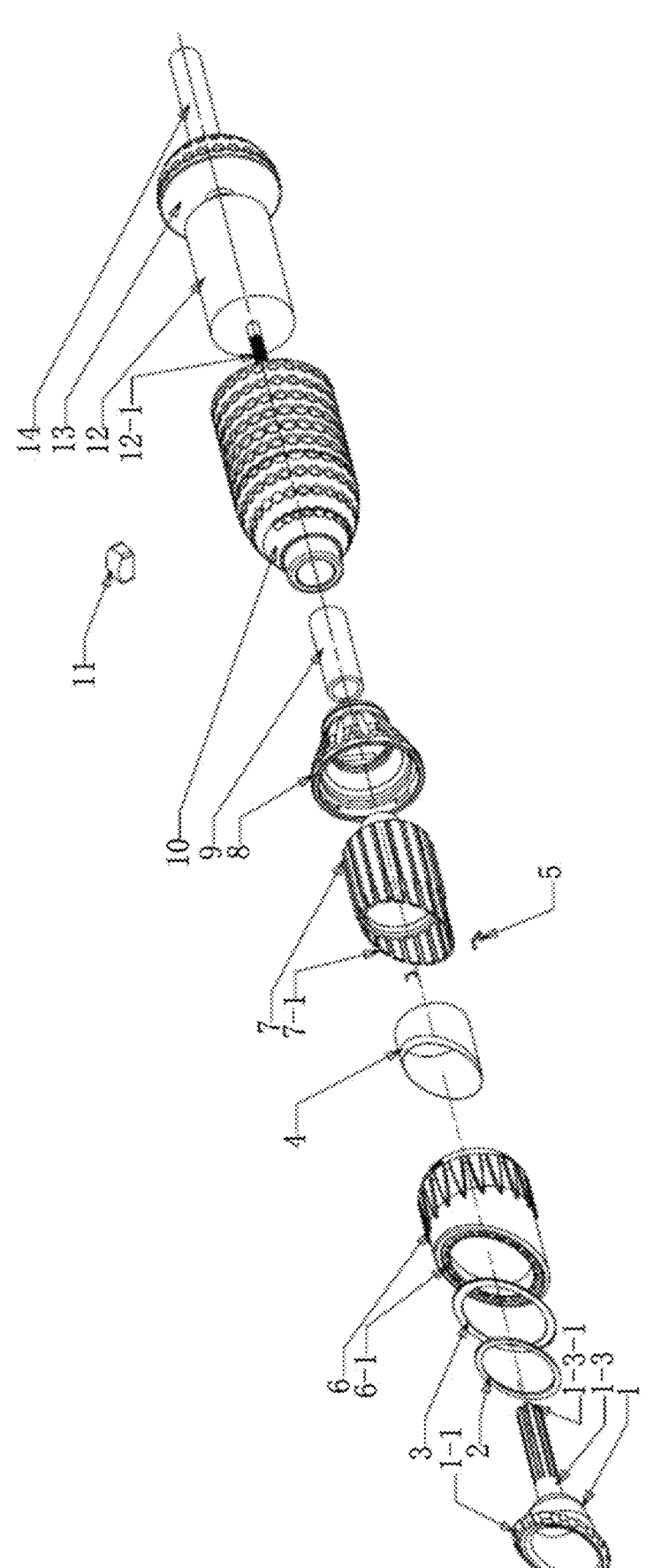
FIG. 9 shows a structurally exploded view of the valgus circumcision device.
Figure 10:
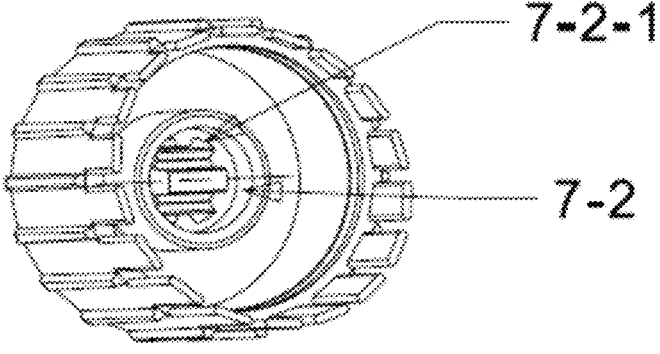
FIG. 10 shows a structural view of a U-nail top ring of the valgus circumcision device.
Figure 11:
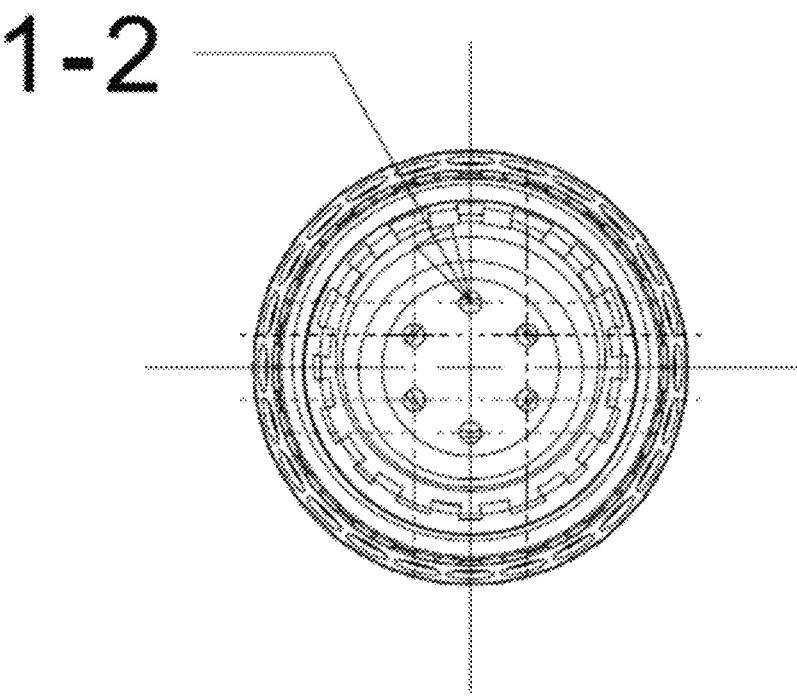
FIG. 11 shows a front end view of the valgus circumcision device.

FIGS. 4 and 10 show detail views of the U-nail top ring of the circumcision device, respectively. Positioning grooves 7-2-1 are formed in the positioning hole 7-2 of the U-nail top ring. FIG. 5 shows a structural view of the circumcision cover provided with a circumcision knife gasket 2 corresponding to a circumcision knife. A U-nail seat 1-4 which is corresponding to the U-nail and configured to chamfer is radially and outwardly arranged on the circumcision knife gasket. Positioning grooves 1-3-1 are formed in the lower end of the circumcision cover. FIG. 6 and FIG. 11 show front end views of the circumcision device, respectively, wherein at least one negative pressure hole 1-2 is formed in the front end.

FIGS. 12-FIG. 17 show preferred embodiments in various embodiments of the present invention.

FIG. 12 and FIG. 16 show an overall appearance view and a stereoscopic view of a valgus circumcision device. It can be seen after adopting a motor for driving, the overall appearance of the circumcision device is simple, and components such as a handle hinge and the like are omitted, so that the mold preparation cost and the production cost are significantly reduced.

FIG. 13 and FIG. 17 show a structural view and a partial enlarged view of the valgus circumcision device, respectively. In the structure shown in the figures, 14 represents a cable, 13 a motor rear shell, 10 a motor front shell, 12 a motor, 11 a switch, 9 a thrust tube, 6 a comprehensive cover, 7 a U-nail top ring, 19 a lower cover, 5 a U-nail, 4 a circumcision knife, 3 a U-nail backing ring, 23 an inner comprehensive cover, 24 a locking ring, 15 an inner ring, and 16 an upper cover. The related driving parts, actuating parts, circumcision parts and the like are of common structures in the art. Referring to the drawings, the position relations and connecting relations are both clear; various combinations in the prior art can be adopted; and the details will not be repeated here. The valgus electric circumcision device comprises a motor 12, a thrust tube 9 and a U-nail top ring 7, wherein the motor 12 is connected to the thrust tube 9, and is configured to drive the thrust tube 9 forward; and the thrust tube 9 is connected to the U-nail top ring 7, and is configured to thrust the U-nail top ring 7 forward. The valgus electric circumcision device also comprises an inner comprehensive cover 23. The motor 12 is connected to the inner comprehensive cover 23. The thrust tube 9 is a hollow cylinder with a first ring-shaped cross section, and the ring-shaped end of the front end of the hollow cylinder is connected to the rear end of the U-nail top ring 7. The U-nail top ring 7 is configured to push out the U-nail 5 from the U-nail groove of the circumcision device. The motor 12 has a connecting rod and an end thread on the connecting rod, and is connected to the inner comprehensive cover 23 via the end thread. The inner comprehensive cover 23 comprises a positioning rod 1-3. Positioning grooves are formed in the positioning rod 1-3, and are provided with inner threads. The inner threads and the end thread are threadedly matched with each other.

The valgus electric circumcision device also comprises a comprehensive cover 6 and a motor front shell 10. The inner comprehensive cover 23 is located in the comprehensive cover. The front end of the motor front shell 10 is connected to the rear end of the comprehensive cover 6. The cross section of the front end of the motor front shell 10 is a second ring capable of accommodating the first ring. The valgus electric circumcision device further comprises: a motor rear shell 13 cooperating with the motor front shell 10 to form a space for accommodating the motor 12, a cable 14 which is connected to and supplies power to the motor 12, and a switch 11 arranged on the motor rear shell 13 or the motor front shell 10 or the comprehensive cover 6 and configured to control the powering on or off and a driving distance and speed of the motor 12. A cable hole is formed in the motor rear shell 13. The cable 14 passes through the cable hole and is connected to the motor 12.

The upper cover 16 and the lower cover 19 cooperates with each other and are locked by the locking ring 24. An inner ring 15 is arranged in the upper cover 16. The inner comprehensive cover 23 is arranged in the lower cover 19. A U-nail backing ring 3 is arranged at the lower end of the inner ring 15, and is corresponding to the U-nail in the U-nail groove. A circumcision knife 4 is arranged beside the U-nail top ring 7, and can be simultaneously pushed out with the U-nail.

Exemplary descriptions are given for the present invention with reference to the drawings in the above. Obviously, the present invention is not limited to the above implementation manners. Any improvement using the methods, concepts and technical solutions of the present invention or direct application of the present invention to other occasions without modifications shall fall into the protection scope of the present invention.

The invention claimed is:

1. A built-in electric circumcision device, comprising: a motor, a thrust tube, a U-nail top ring and a circumcision cover, wherein the motor is connected to or in contact with the thrust tube, and is configured to drive the thrust tube forward; and the thrust tube is connected to or in contact with the U-nail top ring, and is configured to thrust the U-nail top ring forward;

the motor comprises a connecting rod, and the circumcision cover comprises a positioning rod connected to or in contact with the connecting rod;

a front end of the thrust tube is connected to or in contact with a rear end of the U-nail top ring;

the U-nail top ring is configured to push out a U-nail from a U-nail groove of the circumcision device; and the circumcision cover is provided with at least one negative pressure hole.

2. The built-in electric circumcision device of claim 1, wherein the thrust tube is a hollow cylinder with a first ring-shaped cross section; a ring-shaped end of the front end of the hollow cylinder is connected to or in contact with the rear end of the U-nail top ring.

3. The built-in electric circumcision device of claim 2, further comprising a motor front shell and a comprehensive cover, wherein a front end of the motor front shell is connected to a rear end of the comprehensive cover; and/or a cross section of the front end of the motor front shell is in the shape of a second ring capable of accommodating the first ring.

4. The built-in electric circumcision device of claim 3, further comprising a motor rear shell cooperating with the motor front shell to form a space for accommodating the motor.

5. The built-in electric circumcision device of claim 1, wherein the motor is connected to or in contact with the circumcision cover; or the motor has an end thread, and is connected to or in contact with the circumcision cover via the end thread.

6. The built-in electric circumcision device of claim 5, wherein the motor has a connecting rod on which the end thread is arranged.

7. The built-in electric circumcision device of claim 6, wherein the circumcision cover comprises a positioning rod connected to or in contact with the connecting rod or the end thread; and/or a positioning groove is formed in the positioning rod.

8. The built-in electric circumcision device of claim 1, further comprising a cable which is connected to and supplies power to the motor.

9. The built-in electric circumcision device of claim 8, wherein a cable hole is formed in the motor rear shell; and a cable passes through the cable hole and is connected to the motor.

10. The built-in electric circumcision device of claim 1, further comprising a switch which is arranged on a motor rear shell or a motor front shell or a comprehensive cover, and is configured to control the powering on or off, and/or a driving distance, and/or a driving speed of the motor.

11. A valgus electric circumcision device, comprising: a motor, a thrust tube and a U-nail top ring, wherein the motor is connected to or in contact with the thrust tube, and is configured to drive the thrust tube forward; and the thrust tube is connected to or in contact with the U-nail top ring, and is configured to thrust the U-nail top ring forward;

the device further comprises an upper cover, a lower cover, and a locking ring, wherein the upper cover and the lower cover cooperate with each other and are locked by the locking ring;

an inner ring is arranged in the upper cover;

an inner comprehensive cover is arranged in the lower cover;

a U-nail backing ring is arranged at a lower end of the inner ring, and is corresponding to a U-nail in a U-nail groove; and a circumcision knife is arranged beside the U-nail top ring, and is configured to be simultaneously pushed out with the U-nail.

12. The valgus electric circumcision device of claim 11, further comprising an inner comprehensive cover, wherein the motor is connected to or in contact with the inner comprehensive cover.

13. The valgus electric circumcision device of claim 12, wherein the motor has a connecting rod and an end thread on the connecting rod, and is connected to or in contact with the inner comprehensive cover via the end thread.

14. The valgus electric circumcision device of claim 13, wherein the inner comprehensive cover comprises a positioning rod; and a positioning groove is formed in the positioning rod.

15. The valgus electric circumcision device of claim 11, wherein the thrust tube is a hollow cylinder with a first ring-shaped cross section; a ring-shaped end of the front end of the hollow cylinder is connected to or in contact with the rear end of the U-nail top ring; and/or the U-nail top ring is configured to push out a U-nail from a U-nail groove of the circumcision device.

16. The valgus electric circumcision device of claim 15, further comprising a motor front shell and a comprehensive cover, wherein an inner comprehensive cover is located in the comprehensive cover; a front end of the motor front shell is connected to a rear end of the comprehensive cover; and/or a cross section of the front end of the motor front shell is in the shape of a second ring capable of accommodating the first ring.

17. The valgus electric circumcision device of claim 16, further comprising a motor rear shell cooperating with the motor front shell to form a space for accommodating the motor.

18. The valgus electric circumcision device of claim 11, further comprising a cable which is connected to and supplies power to the motor.

19. The valgus electric circumcision device of claim 11, further comprising a switch which is arranged on a motor rear shell or a motor front shell or a comprehensive cover, and is configured to control the powering on or off, and/or a driving distance, and/or a driving speed of the motor.

20. The valgus electric circumcision device of claim 18, wherein a cable hole is formed in a motor rear shell; and the cable passes through the cable hole and is connected to the motor.

\* \* \* \* \*